United States Patent [19]
Bloom et al.

[11] Patent Number: 5,747,299
[45] Date of Patent: May 5, 1998

[54] ANERGY GENES

[75] Inventors: Debra Bloom, Mountain View; C. Garrison Fathman, Portola Valley; Sarah Slaymaker, Stanford, all of Calif.

[73] Assignee: The Board of Trustees of the Leland Stanford Junior University, Stanford, Calif.

[21] Appl. No.: 486,955

[22] Filed: Jun. 7, 1995

Related U.S. Application Data

[63] Continuation-in-part of Ser. No. 265,100, Jun. 23, 1994, abandoned.

[51] Int. Cl.$^6$ .............................. C12P 19/34; C12Q 1/68; G01N 33/00; C07H 21/02
[52] U.S. Cl. ......................... 435/91.2; 435/6; 435/7.1; 436/94; 536/23.1; 536/25.3
[58] Field of Search .................. 204/182.8; 435/6, 435/91.2, 7.1; 436/94; 536/23.1, 25.3

[56] References Cited

PUBLICATIONS

Quill and Schwartz, "Stimulation of Normal Inducer T Cell Clones with Antigent Presented by Purified Ia Molecules in Planar Lipid Membranes," J. Immunol. (1987), 138:3704–3712.

Kuhrober et al., "Vaccination with T Cell Receptor Peptides Primes Anti-Receptor Cytotoxic T Lymphocytes (CTL) and Anergizes T Cells Specifically Recognized by These CTL," Eur. J. Immunol. (1994), 24:1172–1180.

Gregorian et al., "Induction of Peripheral Tolerance with Peptide Specific Anergy in Experimental Autoimmune Neuritis," Cell Immunol. (1993), 150:298–310.

Martin and Davies, "T Cells and Human Autoimmune Thyroid Disease," Thyroid (1992), 2:247–261.

Kang et al., "Transactivation by AP–1 is a Molecular Target of T Cell Clonal Anergy," Science (1992), 257:1134–1138.

LaSalle et al., Early signalling defects in human T–cells anergized by T–cell presentation of autoantigen, J. Exp. Med. v. 176, pp. 177–186, Jul. 1992.

Mastrogiacomo et al., Cysteine string proteins: a potential link between synaptic vesicles and presynaptic Ca2+ channels, Science v. 263, pp. 981–982, Feb. 1994.

Liang et al., Differential display of eukaryotic messenger RNA by means of the polymerase chain reaction, Science v. 257, pp. 967–971, Aug. 1992.

Ronchese et al., Functionally distinct subsites on a class II major histocompatability complex molecule, Nature v. 329, pp. 254–256, Sep. 1987.

Sloan–Lancaster et al., Induction of T–cell anergy by altered T–cell receptor ligand on live antigen presenting cells, Nature v. 363, pp. 156–159, May 1993.

Kennedy et al., Specific immune regulation of chronic relapsing experimental allergic encephalomyelitis in mice, Journal of Immunology, v. 141, pp. 2986–2993, Nov. 1988.

*Primary Examiner*—George G. Elliott
*Assistant Examiner*—Andrew Wang
*Attorney, Agent, or Firm*—Fish & Richardson P.C.; Bret E. Field; Pamela J. Sherwood

[57] ABSTRACT

Methods and compositions are provided for identifying genes associated with induction of anergy in T-cells and the use of the nucleic acids or proteins as diagnostics for monitoring induction of tolerance for the presence of tolerized T-cells in a physiological sample, or elucidating the pathway to anergy or activation in T-cells. A cysteine string protein is found to indicate quiescent T-cells and is lost with anergic T-cells.

4 Claims, 2 Drawing Sheets

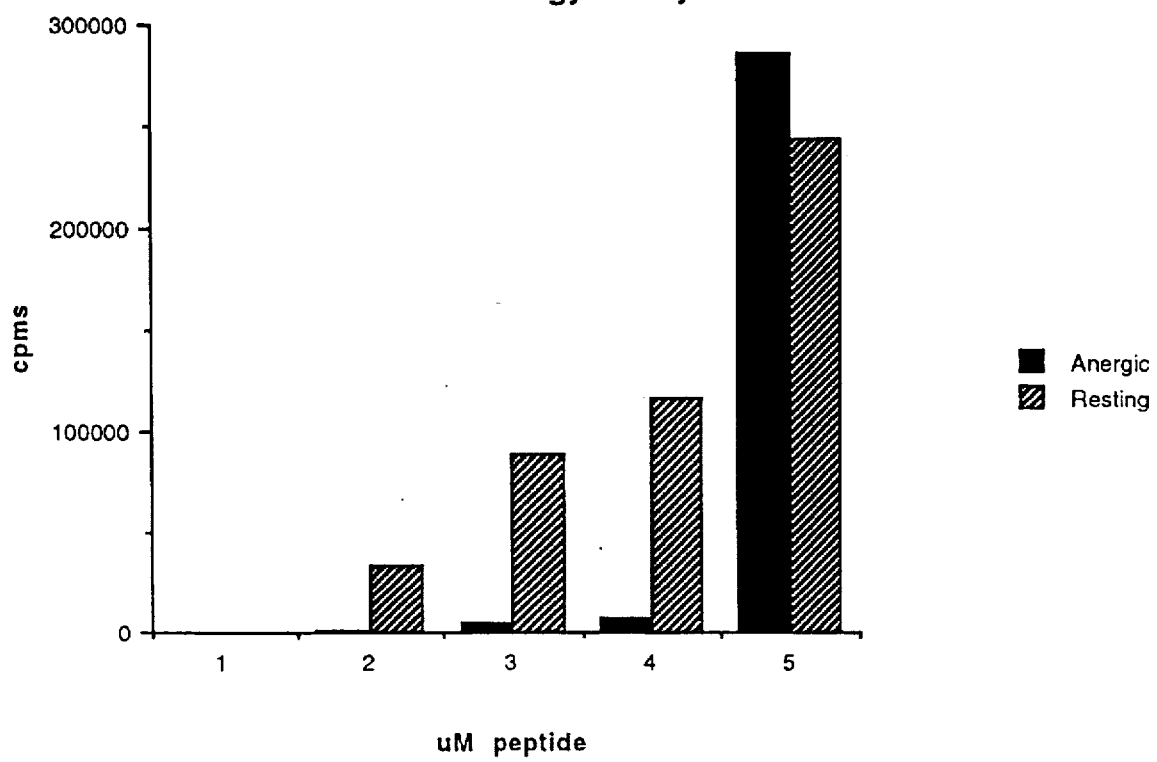

Figure 2

CYSTEINE STRING PROTEIN

```
                                        27                                          54
ATG GCT GAC CAG AGG CAG CGC TCA CTC TCT ACT TCC GGG GAA TCG TTA TAC CAT
 M   A   D   Q   R   Q   R   S   L   S   T   S   G   E   S   L   Y   H 81                                         108
GTT CTT GGA CTG GAC AAG AAT GCA ACC TCA GAT GAC ATT AAA AAG TCC TAT CGG
 V   L   G   L   D   K   N   A   T   S   D   D   I   K   K   S   Y   R 135                                         162
AAG CTG GCC CTG AAG TAT CAC CCT GAC AAG AAC CCT GAT AAC CCA GAG GCT GCA
 K   L   A   L   K   Y   H   P   D   K   N   P   D   N   P   E   A   A 189                                         216
GAC AAG TTT AAG GAG ATT AAC AAC GCA CAC GCC ATC TTG ACA GAC GCC ACG AAA
 D   K   F   K   E   I   N   N   A   H   A   I   L   T   D   A   T   K 243                                         270
AGA AAC ATT TAT GAC AAG TAT GGC TCG CTG GGG CTC TAT GTG GCG GAG CAG TTT
 R   N   I   Y   D   K   Y   G   S   L   G   L   Y   V   A   E   Q   F 297                                         324
GGG GAG GAG AAC GTC AAC ACC TAC TTC GTA CTC TCC AGC TGG TGG GCC AAG GCG
 G   E   E   N   V   N   T   Y   F   V   L   S   S   W   W   A   K   A 351                                         378
CTG TTT GTT GTT TGT GGC CTC CTC ACC TGC TGC TAC TGC TGC TGC TGT TTG TGC
 L   F   V   V   C   G   L   L   T   C   C   Y   C   C   C   C   L   C 405                                         432
TGT TGC TTT AAC TGC TGC TGT GGG AAA TGC AAG CCC AAG GCA CCT GAG GGT GAG
 C   C   F   N   C   C   C   G   K   C   K   P   K   A   P   E   G   E 459                                         486
GAG ACA GAA TTC TAC GTA TCC CCT GAA GAC TTG GAG ACA CAG CTG CAG TCT GAT
 E   T   E   F   Y   V   S   P   E   D   L   E   T   Q   L   Q   S   D 513                                         540
GAA AGG GGA GGG CAC TGA CAC TGT GCC GAG AGT GTT TGT GCT GGC ATC TGG GAC
 E   R   G   G   H   .   H   C   A   E   S   V   C   G   G   I   W   D 567                                         594
TGT TGA GGT GTG AAC GTC GAC ACT TGA GAG GCT ACA GAC ACA CCG ATC GTC ATA
 C   .   G   V   N   V   D   T   .   E   A   T   D   T   P   I   V   I 621                                         648
CAG CCA GCA TCT GCC ACA GAG ACC ACC CAG CTG ACA GCT GAC TCC CAC CCC AGC
 Q   P   A   S   A   T   E   T   T   Q   L   T   A   D   S   H   P   S

TAT CAC ACC GAC GGG TTC AAC TAA
 Y   H   T   D   G   F   N   .
```

ANERGY GENES

CROSS-REFERENCE TO RELATED APPLICATIONS

This application is a continuation-in-part of application Ser. No. 08/265,100, now abandoned, filed Jun. 23, 1994.

INTRODUCTION

1. Technical Field

The field of this invention is modulation of T-cell response.

2. Background

The immune system is the major surveillance for detecting disease states as a result of pathogenic invasion, cellular aberration as involved with neoplasia and psoriatic lesions, or other foreign bodies. The T-cell can act directly to protect a mammalian host, but may also cooperate with other cells such as B-cells, to further enhance protective mechanisms. The T-cell has a number of mechanisms available to it that result in cellular destruction of a target, and, therefore, numerous mechanisms have evolved to prevent the T-cell from attacking the host.

The thymus has evolved mechanisms whereby T-cells which might attack native tissue are depleted so that only T-cells capable of attacking other than native tissue are allowed to mature. The process of clonal deletion has been found to have a small but significant incidence of failure, as is evidenced by numerous autoimmune diseases, such as diabetes, lupus, rheumatoid arthritis, myasthenia gravis, multiple sclerosis, and the like. In these instances, it is necessary to find ways to inhibit the T-cell attack on the native tissue.

T-cells are also active in recognizing allogeneic tissue and attacking such tissue, which is a problem in the case of transplantation. This has required the use of immunosuppressants, which have a substantial range of side effects, as well as leaving the host vulnerable to opportunistic infection. In instances where T-cells are transferred to a patient from a donor, graft-versus-host disease is frequently observed. Again, there is substantial interest in inhibiting T-cell activity in these situations.

Besides the mechanism of clonal deletion, there is believed to be a further mechanism for diminishing specific T-cell activity, referred to as anergy. The present wisdom suggests that T-cell stimulation requires co-stimulation and that in the absence of co-stimulation, antigen presentation may result in anergy, where the T-cell becomes tolerized to the antigen and is not stimulated upon a subsequent encounter with the antigen.

The ability to induce anergy, which may be relatively limited in time, and may be specific to particular T-cells, is a very attractive alternative to present day methods of immunosuppression. Even if all T-cells or only helper or suppressor T-cells were made anergic, this would still leave a substantial number of branches of the immune system active. Furthermore, by limiting the anergic state to a particular subset of T-cells, one would maintain the immune system substantially intact, while precluding those undesired aspects of T-cell activity. There is, therefore, substantial interest in developing methodologies for inducing anergy where T-cell activation is undesired.

RELEVANT LITERATURE

Liange and Pardee, Science (1992) 257, 967–971, describe differential display. Quill and Schwartz, J. of Immunol. (1987) 136, 3704–3712, describe induction of anergy using purified MHC in planar lipid membranes.

Articles associated with cysteine string proteins include Mastrogiacomo and Gundersen, Molecular Brain Research (1995) 28, 12–18; Ginetzky, BioEssays (1994), 16, 461–463 and references cited therein; and Mastrogiacomo et al., J. Neurochemistry (1994) 62, 873–880.

SUMMARY OF THE INVENTION

Nucleic acid and protein compositions are provided associated with the anergic state of T-cells. The compositions find use in elucidating the anergic state, identifying the agents associated with induction of the anergic state, screening compounds capable of regulating the anergic state, screening cell populations for tolerized T-cells, and providing opportunities for release of T-cells form the anergic state. The proteins may be used to produce antibodies, where the antibodies and DNA probes may be used in diagnosis for analyzing the anergic and/or active T-cell repertoire of a mammalian host. Exemplary of genes associated with the anergic state is a cysteine string protein associated with the resting T-cell population, as distinct from the anergic T-cell, where the gene is not expressed.

BRIEF DESCRIPTION OF THE DRAWINGS

FIG. 1 is a graph showing the results of an anergic assay with increasing concentrations of peptide.

FIG. 2 is the amino acid and nucleic acid sequence of a mouse cysteine string protein (SEQ ID NO:06).

DESCRIPTION OF SPECIFIC EMBODIMENTS

Nucleic acid and protein compositions are provided, here the nucleic acids and proteins are associated with the anergic and unresponsive state of T-cells. The proteins are found to be expressed specifically in anergic T-cell clones as distinct from quiescent T-cell clones and activated T-cell clones. The T-cell clones may be CD4+ or CD8+, particularly CD4+.

The subject invention is applicable with any mammalian host that has T-cells, including domestic animals, such as bovine, ovine, canine, equine, lagomorpha, feline, murine, etc., primates, such as gorillas, monkeys, humans, and the like.

Evidence of the anergic state is the absence of a cysteine string protein having at least about 80% homology (as defined by FASTP) with the human sequence fragment (SEQ ID: No 6).

The anergic and unresponsive state may be induced in T-lymphocytes by presentation of an antigen by a cell other than a normal antigen presenting cell (APC), which has been transfected with major histocompatibility complex antigen by which a selected T-cell clone is restricted. Resting T-cells are provided with an appropriate peptide recognized by the resting T-cells in the context of the MHC transfected into a cellular host other than an APC. The MHC is expressed as a result of introduction into a mammalian cell other than an antigen presenting cell of genes constitutively expressing the α and β chains of the MHC, particularly class II MHC. A wide variety of cell types may be used for integration of the genes coding the MHC subunits, including such cells as fibroblasts, where the cells may be grown in culture and may be normal or neoplastic. Importantly, these cells do not provide other proteins, either cell surface proteins or secreted proteins, associated with antigen presenting cells, which together with the MHC and peptide result in co-stimulatory signals.

The T-cell clones which were employed are identical as being recognized by the resting T-cells in the context of he MHC by which the T-cells are restricted. The cells are combined in an appropriate medium, e.g. RPMI with 10% fetal calf serum (FCS), non-essential amino acids and β-mercaptoethanol, where the numbers of each of the cells will generally be in the range of about $1 \times 10^4$–$1 \times 10^6$ in a volume of about 0.1–1 ml. The peptide concentration will generally be in the range of about 2–20 μM, usually 7–10 μM. In parallel cultures, T-cells and the MHC expression cells are incubated without peptide.

After from about 10–36 hours of incubation, the T-cell populations are separated from the MHC expressing cells. This is readily achieved by incubating the cells with anti-CD4 coupled microbeads, although other T-cell markers such as CD7 and CD3 or T-cell receptor proteins may also serve for the separation. For class 1 MHC restricted T-cells one can use CD8, as well as the other common T-cell markers. With the microbeads, one may use a magnetic column for passaging the beads and then carefully washing with buffer, so as to remove any non-specifically bound cells. Instead of microbead separation, one may use panning, fluorescence activated cell sorting, affinity columns, or plates, or the like, to purify the T cell population.

After isolating the specifically bound T-cells from the different cultures, one should have a population which is at least about 95% pure, preferably at least 99% pure. Each of the culture is then assayed for its ability to respond to peptide presented by normal antigen presenting cells, particularly splenocytes. The cultures are prepared in substantially the same way as described above, except that antigen presenting cells, such as monocytes, macrophages, B-cells, or the like, or combinations thereof may be employed. The cultures are incubated for about 48 hours, pulsed with tritiated thymidine and incorporation measured about 18 hours later. The absence of incorporation above control levels, where the T-cells are presented with antigen presenting cells which do not stimulate the T-cells, either due to using an MHC to which the T-cells are not restricted or using a peptide to which the T-cells are not sensitive, is indicative of an absence of activation. One may use other conventional assays to determine the extent of activation, such as assaying for IL-2, -3, or -4, cell surface proteins associated with activation, e.g. CD71 or other convenient techniques.

cDNA libraries may then be prepared from each of the cultures in accordance with conventional methods. Messenger RNA is isolated, reverse transcribed using an appropriate reverse transcriptase and poly dT primer, followed by preparation of the complementary sequence by denaturing the DNA-RNA complex strands and copying the DNA sequence with DNA polymerase and the appropriate nucleotide triphosphates.

The dsDNA may then be inserted into appropriate vectors for cloning and preparation of a cDNA library.

For determining which genes are associated with anergy, anergy genes are found to be capable of detection by differential display. Differential display is performed by generating cDNA from polyA+ mRNA from anergic and nonanergic T-cell counterparts. This is performed by reverse transcription of the polyA+ mRNA with an oligo dT primer, which contains two variable anchor nucleotides at the 3'end, (e.g. [SEQ ID NO:1] $T_{11}$ CA, and [SEQ ID NO:2] $T_{12}$ GC). The primer anneals and is extended only with those mRNA's that contain the specific dinucleotide sequence adjacent to the 5'-terminus of the polyA region. Annealing at about 42° C. in standard reverse transcriptase buffer, usually including about 50 mM KCl or NaCl, for 60 minutes provides the desired degree of sensitivity.

For the most part, the primers will be at least 10 nucleotides, more usually no more than about 15 nucleotides, where one will have any of the combinations of the four nucleotides at the 3' terminus and at least about 8 deoxythymidines. After reverse transcription, the resulting cDNA populations are amplified using the polymerase chain reaction (PCR) in accordance with conventional conditions. Usually amplification will involve at least 10 cycles and not more than about 40 cycles, using the same oligo dT 3'-primer and a 5'-primer which has been designed to amplify a limited number of CDNA species resolvable on a typical gel, particularly a sequencing gel. The 5' primer will generally be from about 8 to 10 nucleotides and will include various common 4 and 5 nucleotide sequence combinations. By virtue of the different sites at which the 5' primer hybridizes, one will obtain a variety of different sized ssDNA strands corresponding to the different mRNAs. Generally the ssDNAs will be less than about 1 knt, usually less than about 500 nt, and usually at least about 35 nt, more usually at least about 50 nt. By end labeling the 3'PCR-primer, differences in the mRNA species can be visualized on a gel.

Bands unique to the anergized population are then excised and eluted from the gel, amplified once again in order to obtain enough cDNA for cloning purposes, and then cloned directly into a convenient cloning vector, e.g. the vector "PCR1000" (Invitrogen). The vector is then introduced into a suitable host strain, and sufficient DNA produced to determine the sequence of the insert. These sequences may then be used as probes to retrieve full length cDNA's from an anergic T-cell cDNA library prepared as described above. With murine 11.3.7. T-cells which have been anergized, it is found that a combination of primers using Ldd1 [SEQ ID NO:3] for the 5' terminus (GACTAGGTAC) and $T_{12}$GC for the 3' terminus provides for a plurality of bands in the anergized cells, which are absent from the quiescent and activated T-cells. By contrast, the combination of Ldd1 and $T_{11}$ CA did not provide any different bands between bands between the anergized and quiescent T-cells.

Northern blots to detect the presence of the transcription products of genes associated with anergy may be performed using the gel eluted DNA described above as a probe. The messenger RNA for the northern blot will be isolated by conventional techniques from T-cell cultures as previously described. A wide variety of techniques are available for fractionating mRNA, e.g. gel electrophoresis, capillary electrophoresis, and the like, where by hybridizing with labeled subject DNA probes, one can detect the presence of the target mRNA.

The subject probes can also be used in research to elucidate the mechanism of anergy and how a T-cell distinguishes between stimuli which result in anergy and stimuli which result in activation. The sequence of the genes may also be used in preparing antisense sequences, where individual genes associated with anergy may be inhibited for the elucidation of the anergic response.

The bands from the gels may be eluted, e.g. electroeluted and used as immunogens in accordance with known conventional ways to produce antisera and monoclonal antibodies. See, for example, *Antibodies: A Laboratory Manual*, EDS. Ed Harlow, David Lane, Cold Spring Harbor Laboratory, Coldspring Harbor, N.Y., 1988. Briefly, mouse or other convenient laboratory mammal may be immunized with a protein, normally in conjunction with an adjuvant and one or more booster shots may be employed at 2–6 week intervals. The spleen may be removed and the splenocytes may be immortalized by any convenient means, e.g. fusion with a myeloid cell line, transformation, or the like. The resulting immortalized cells, e.g. hybridomas, may then be screened for antibodies specific for the immunogen.

The antibodies may be used for determining anergized, as distinct from active or quiescent T-cells. By isolating T-cells which have a specific affinity for a peptide associated with a particular MHC, one can screen a patient to determine whether the patient has been tolerized, for example, in relation to an autoimmune disease, transplanted organ or the like. The cells specific for the peptide which are expressing the proteins associated with anergy may be identified in accordance with conventional immunoassays, where the antibody may be labeled with an enzyme, fluorescer, radioisotope, etc., and the proteins of the cell lysate bound to the surface. By contacting the surface with a labeled antibody, the anergic state of the cell may be determined.

The cDNA obtained from the anergic gel may be expanded using PCR and then used as probes in assays for anergic cells. Thus, T-cells may be screened in a variety of diseases, such as autoimmune diseases, where their host is particularly susceptible to one or more pathogenic diseases, due to anergy, whether a host will be more or less tolerant to a transplanted organ due to anergy, whether a vaccine may be more or less effective due to anergy, and the like. By taking a blood sample, isolating T-cells, using T-cell specific markers as described above, providing for presenting cells with a peptide or peptides of interest, one may be distinguished between quiescent, activated and anergic T-cells. Of particular interest is screening the host T-cells, after one has attempted to tolerize the host to one or more antigens.

The T-cells may be isolated as described above, the message RNA isolated by conventional techniques and Northern blots employed to detect the presence of the transcription products of the genes associated with anergy. A wide variety of techniques are available for separating massage RNA, e.g. gel electrophoresis, capillary electrophoresis, and the like, whereby hybridizing the subject DNA probes, where the probes are labeled one can detect the presence of the target message.

The subject probes can also be used in research to elucidate the mechanism of anergy and how a T-cell distinguishes between stimuli which result in anergy and stimuli which result in activation. The sequence of the genes may also be used in preparing antisense sequences, where individual genes associated with anergy may be inhibited for the elucidation of the anergic response. The antisence DNA sequences may use natural nucleotides or unnatural nucleotide mimics, where oxygens of the phosphate may be replaced with sulfur, methylene groups, amino groups, or the like, unnatural sugars may be used, or the phosphate esters may be substituted entirely by a different backbone, e.g. polypeptide. The antisense molecules may be administered by fusion with liposomes, where the antisense molecules are present in the lumen, particularly where one uses fusion proteins, such as proteins of the Sendai virus, by allowing for diffusion across the cell membrane, etc.

The cDNA obtained from the differential display on a gel of anergic sequences may be expanded using PCR and then used as probes in assays for anergic cells. Thus, T-cells may be screened in a variety of diseases, such as autoimmune diseases, where the host is particularly susceptible to one or more pathogenic diseases, due to anergy, whether a host will be more or less tolerant to a transplanted organ due to anergy, whether a vaccine may by more or less effective due to anergy, and the like. By taking a blood sample, isolating T-cells,using T-cell specific markers as described above, providing for presenting cells with a peptide or peptides of interest, one may distinguish between quiescent, activated and anergic T-cells. Of particular interest is screening host T-cells after one has attempted to tolerize the host to one or more antigens.

For the most part, the physiologic samples employed will be blood or a blood derivative, e.g. plasma or serum, but samples may also involve other sources of T-cells, particularly where T-cells may be invasive. Thus other sites of interest may be tissues or fluids associated therewith, as in the brain, lymph node, neoplasm, spleen, liver, kidney, pancreas, tonsil, thymus, joint, synovia, and the like. The sample may be used as obtained or may be subject to modification, as in the case of extraction, dilution, purification, concentration, or the like. Cells may be lysed and the lysate used, or DNA and/or proteins isolated. T-cells may be isolated or concentrated. The particular manner of treating the sample will depend on the nature of the sample and the particular procedure being employed for the assay.

The bands from the gels or the genes identified using the bands as probes may be used to identify and isolate the protein. Where the band is in the untranslated region, the band may be used as described above to isolate a cDNA gene, which may be wholly or partially sequenced. The nucleic acid sequence may be used to prepare oligopeptides by synthesis or the entire protein by recombinant technology, preparing an expression cassette with the gene for use in an appropriate expression host. The protein may then be isolated and purified, generally to at least about 50% pure, usually at least about 90% pure, and preferably substantially completely pure. By pure is intended free of other proteins with which the protein is naturally found. In some instances, the DNA may be fused at its 3' terminus to a marker gene to provide a fusion protein, where isolation and purification may be achieved by virtue of the properties of the marker gene, e.g. β-galactosidase. These techniques are sufficiently common, and do not require exemplification here. See, for example, Sambrook et al., Molecular Biology: A Laboratory Manual, Cold Spring Harbor Laboratory, New York, 1989.

Agents and drugs can be screened for their effect in inhibiting or producing anergy. By combining cells with the agent under conditions where anergy is induced, one can screen cells for the presence or absence of proteins or mRNA related to anergy. In this way can quantitate the effect of such agents or drugs on anergy induction.

Cysteine string proteins are characterized by having a string of cysteine residues clustered in one small region flanked by a very polar amino N-terminal region and a polar carboxy containing C-terminal region. The protein is palmitoylated, so as to have a strongly hydrophobic region associated with the cysteine string. The cysteine string proteins are found to have a J region in the N-terminal portion which binds to Hsp 70. The cysteine string protein is associated with neuronal tissue and is associated with synaptic vesicles. The protein has a molecular weight in the range of about 25 to 30 kDa when completely palmitoylated, where loss of all palmitoyl groups can result in a reduction in from about 2500 to 7500 Dal. The protein is expressed in resting T-cells, but not in anergized cells.

The peptide fragments or protein may be used to produce antibodies by using the peptide fragment or protein as an immunogen, where the peptide may be conjugated to an immunogenic carrier. See, for example, Antibodies: A Laboratory Manual, eds. Ed Harlow, David Lane, Coldspring Harbor Laboratory, Coldspring Harbor, N.Y., 1988. Briefly, a mouse or other convenient laboratory mammal may be immunized with a protein, normally in conjunction with an adjuvant and one or more booster shots may be employed at 2–6 week intervals. The spleen may be removed and the splenocytes may be immortalized by any convenient means, e.g. fusion with a myeloma cell line, transformation, or the like. The resulting immortalized cells, e.g. hybridomas, may then be screened for antibodies specific for the immunogen.

The antibodies may be used for determining anergized, as distinct from active or quiescent T-cells. By isolating T-cells which have a specific affinity for a peptide associated with a particular MHC, for example, using antigen presenting cells bound to a surface in conjunction with the peptide of interest and then isolating the T-cells which are specifically bound, one can screen a patient to determine whether the patient has been tolerized, for example, in relation to an autoimmune disease, transplanted organ, or the like. The cells specific for the peptide which are expressing the proteins associated with anergy may be identified in accordance with conventional immunoassays, where the antibody may be labeled with an enzyme, fluorescer, radioisotope, etc., and the proteins of the cell lysate bound to a surface. By contacting the surface with a labeled antibody, the anergic state of the cell may be determined.

The subject invention may find application in inducing anergy in the case of autoimmune diseases. By isolating the cells from a host, e.g. by plasmapheresis and T cell selection, one may induce anergy in the same way as described in the subject invention, by presenting the peptide associated with the autoimmune disease in the context of an MHC antigen to which the T-cells are restricted in the absence of at least one component necessary to stimulation of the T cell, e.g. using a cell other than an APC, transformed with genes which express the subunits of the MHC. A representative sample of the cells which bind to the presenting cells may then be screened for the expression of the genes associated with anergy.

The proteins expressed by those genes associated with anergy which result in the presence of surface membrane proteins offer opportunities to isolate anergic T-cells. Thus, the antibodies prepared as described above may be used to isolate anergic T-cells. By labeling the appropriate antibody, particularly a monoclonal antibody, one may separate the anergic cells from the other T-cells. For example, with a fluorescer labeled antibody, a fluorescence activated cell sorter may be used for isolation of the anergic T-cells; with magnetic bead labeled antibodies, one may use magnetic separation; etc.

To the extent that the nucleic acids or proteins, including antibodies, may find prophylactic or therapeutic use in a host, they will normally be administered parenterally, orally or by inhalation, particularly intravascularly. Various physiologically acceptable carriers may be employed, either liquid or solid, such as saline, aqueous ethanol, glycerol, phosphate buffered saline, vegetable oils, sugar, alum, etc. Depending upon the host indication, the composition used, its range of efficacy and the model and regimen of administration, the amount of the compound will vary widely and can be determined empirically, as is known in the art. Usually an animal model will be used to define a range of interest and safety, and the compound may then be investigated in humans for safety, followed by evaluation for efficacy. The subject compositions may find use in transplantation, treatment of autoimmune diseases, cancer therapies and chronic infectious diseases, etc.

The following examples are offered by way of illustration and not be way of limitation.

EXPERIMENTAL

Isolation of Anergic T-cell Clones: Two Class II restricted mouse T-cell clones, 11.3.7 and 12.2 (described in Danska, et al. [1992] J.E.M. 172:27–33, The presumptive CDR3 regions of both T cell receptor α and β chains determine T cell specificity for myoglobin peptides) were employed. The clones are specific for sperm whale myoglobin residues 110–121 presented in the context of $E_\alpha^d A_\beta^d$. Anergy was induced by combining 50,000 cells/well in a 96 well microtiter plate of clone 11.3.7 or 12.2 with 50,000 of L-cell transfectants, which had been transfected with, and were expressing,the genes encoding $E_\alpha^d A_\beta^d$, where the mixed Class II haplotype was expressed on the cell surface. The medium employed was RPMI, 10% FCS, non-essential amino acids and β-mercaptoethanol, comprising 10 μM of the sperm whale myoglobin 110–121 peptide. The cellular composition is incubated for 24 hours.

The T-cells are then isolated by a method described in the manufacturer's protocol for Mini-Macs (Miltenyi Biotec, Inc.) Specifically, magnetic microbeads coupled with anti-CD4 (purchased from Milteny Biotech, Inc., Sunnyvale, Calif.) were added to the cell medium described above, and then separated on a magnetic column according to the manufacturer's protocol. The above-described procedure was repeated for a parallel culture, where the T-cells and the L-cells were incubated without the peptide.

The collected anergic and nonanergic T-cells were then assayed for their ability to respond to peptide presented by splenic (professional) APC's. 50,000 T-cells are added to $5 \times 10^5$ irradiated mouse DBA/2 splenocytes in 96 well plates. Duplicate plates are set up with increasing peptide concentrations added (i.e. 0,0.1,1,10 µM 110–121 peptide). IL-2 is added as a control for T cell viability. The above cultures were incubated for 48 hours, followed by pulsing with 1 µCi/well $^3$H-thymidine, and incorporation of the thymidine measured 18 hours later.

Gene Identification: Candidate anergy genes were identified using differential display (Liang and Pardee, *Science* (1992) 257, 967–971). cDNA from 0.5 µg of polyA+mRNA from the anergic and nonanergic T-cell counterparts was generated. The generation employed reverse transcription with an oligo dT primer, which contains two variable anchored nucleotides at the 3' end, e.g. [SEQ ID NO:1] $T_{11}$CA and [SEQ ID NO:2] $T_{12}$GC. The conditions employed are described in Liang and Pardee, supra. The reverse transcription is performed substantially as described in Molecular Cloning: *A Laboratory Manual*, Second Edition, Sambrook et al. eds., Cold Spring Harbor Laboratory Press, Cold Spring Harbor, N.Y., 1989, Chapter 8. The resulting cDNA populations are amplified using the polymerase chain reaction (PCR) using combinations of the poly dT primer and the 5' primer Ldd1 [SEQ ID NO:3] (5'-CTGATCCATG) or Ldd2 [SEQ ID NO:4] (5'-CTGCTCTCA). The conditions for the PCR were A) 1 cycle: 95° for 5 min. and B) 40 cycles: 95° for 30 sec., 40° for 1 min, 72° for 1 min and a final incubation at 72° for 5 min. The 3'-PCR primer was end labeled with $^{32}$P-ATP to allow for visualization of the DNA sequences on a sequencing gel. A comparison was made of lanes obtained from the anergic cells with lanes obtained from the quiescent cells.

The unique bands of the anergized population are excised from the gel and eluted from the gel, followed by amplification using PCR to increase the available cDNA. The cDNAs are labeled with radioisotopes and used to screen a cDNA library from the anergic T-cells. Clones having cDNAs which hybridize are expanded, the cDNAs isolated and sequenced.

Results

The in vitro anergy system is found to consistently give a 90–95% reduction in proliferation of the anergized 11.3.7 T-cells versus their resting counterparts. After passage of the anti-CD4 bound T-cells over the magnetic column, greater than 99% purity is achieved resulting in minimal contamination by L-cells.

The combination of primers Ldd1 [SEQ ID NO:3] and $T_{12}$GC [SEQ ID NO:1] revealed several bands in the anergy lane that were not visibly present in the resting lane, shown in FIG. 1. The other combinations such as Ldd1 [SEQ ID NO:3] and $T_{11}$CA [SEQ ID NO:2] showed identical band patterns between the anergic cells and quiescent cells.

As controls, to assure the L-cells or a minority of activated T-cells in the anergized population were not contributing to the unique bands, MRNA from pure populations of L-cells and activated at 11.3.7 T-cells were isolated. After amplification of the cDNA using the same primers, the controls were run adjacent to the anergized and resting T-cell PCR products demonstrating that the bands unique to the anergized populations were not due to other "contaminating" cells.

Table 2 shows the sequence [SEQ ID NO:5] of a fragment isolated according to the above procedures.

```
5'-GAC TAG GTA CCG TAC AGT TTC ATA CAC TGA GAC AGT TCT TTG
   TGT AGT TTC TGT TGA ACC GAG ACG ATC CAA ATT TCT AAC ATT
   CCT ACC ACT GTC CGG GTG TAC AGA CAG TCT CAA TAA GAG AGA
   CGT TCG TGA ATC TAG TTT CGG GAG TGA GGA TTG GAA TCG TCA
   AAG TAA TTG TCG GGA CAT TAA GAA GTG TTT AAT CTA TAT AAG
   CAC TAC AAA ATT TAG AGT GTC AGA TGG TAA TAG TCA CGT TTT
   TTT TTT TT-3'
```

Following the procedures described above, a mouse cysteine string protein cDNA was identified and sequenced. The nucleic acid sequence and putative amino acid sequence are set forth in FIG. 2.

In accordance with the subject invention, anergic cells can be screened and tolerizing monitored by detecting the transcription or expression of particular genes, individually or in combination. Furthermore, by having available the sequences encoding the genes associated with anergy and the proteins associated with anergy, one can prepare reagents which will allow for the elucidation of the mechanisms associated with induction of tolerance or activation.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for identifying anergic T-cells in a T-cell composition subjected to a T-cell activating agent, said method comprising:

detecting expression of cysteine string protein by said T-cells, whereby the absence of expression is indicative of anergy.

2. A method according to claim 1, wherein said detecting is by a nucleic acid probe for cysteine string protein mRNA.

3. A method according to claim 1, wherein said detecting is with an antibody to cysteine string protein.

4. A method according to claim 1, comprising the further step prior to detection of, adding a candidate agent to said T-cell composition;

whereby the effect of said agent on induction of anergy is determined.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:1:

TTTTTTTTTT TCA                                              13

( 2 ) INFORMATION FOR SEQ ID NO:2:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:2:

TTTTTTTTTT TTGC                                             14

( 2 ) INFORMATION FOR SEQ ID NO:3:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:3:

CTGATCCATG                                                  10

( 2 ) INFORMATION FOR SEQ ID NO:4:

( i ) SEQUENCE CHARACTERISTICS:
    ( A ) LENGTH: 9 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:4:

CTGCTCTCA                                                   9

( 2 ) INFORMATION FOR SEQ ID NO:5:

( i ) SEQUENCE CHARACTERISTICS:
    ( A ) LENGTH: 260 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:5:

```
GACTAGGTAC CGTACAGTTT CATACACTGA GACAGTTCTT TGTGTAGTTT CTGTTGAACC    60

GAGACGATCC AAATTTCTAA CATTCCTACC ACTGTCCGGG TGTACAGACA GTCTCAATAA   120

GAGAGACGTT CGTGAATCTA GTTCGGGAG TGAGGATTGG AATCGTCAAA GTAATTGTCG   180

GGACATTAAG AAGTGTTTAA TCTATATAAG CACTACAAAA TTTAGAGTGT CAGATGGTAA   240

TAGTCACGTT TTTTTTTTT                                                260
```

(2) INFORMATION FOR SEQ ID NO:6:

(i) SEQUENCE CHARACTERISTICS:
        (A) LENGTH: 672 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
ATGGCTGACC AGAGGCAGCG CTCACTCTCT ACTTCCGGGG AATCGTTATA CCATGTTCTT    60

GGACTGGACA AGAATGCAAC CTCAGATGAC ATTAAAAAGT CCTATCGGAA GCTGGCCCTG   120

AAGTATCACC CTGACAAGAA CCCTGATAAC CCAGAGGCTG CAGACAAGTT TAAGGAGATT   180

AACAACGCAC ACGCCATCTT GACAGACGCC ACGAAAAGAA ACATTTATGA CAAGTATGGC   240

TCGCTGGGGC TCTATGTGGC GGAGCAGTTT GGGGAGGAGA ACGTCAACAC CTACTTCGTA   300

CTCTCCAGCT GGTGGGCCAA GGCGCTGTTT GTTGTTTGTG GCCTCCTCAC CTGCTGCTAC   360

TGCTGCTGCT GTTTGTGCTG TTGCTTTAAC TGCTGCTGTG GGAAATGCAA GCCCAAGGCA   420

CCTGAGGGTG AGGAGACAGA ATTCTACGTA TCCCCTGAAG ACTTGGAGAC ACAGCTGCAG   480

TCTGATGAAA GGGGAGGGCA CTGACACTGT GCCGAGAGTG TTTGTGGTGG CATCTGGGAC   540

TGTTGAGGTG TGAACGTGGA CACTTGAGAG GCTACAGACA CACCGATCGT CATACAGCCA   600

GCATCTGCCA CAGAGACCAC CCAGCTGACA GCTGACTCCC ACCCAGCTA TCACACCGAC   660

GGGTTCAACT AA                                                       672
```